United States Patent
Hashimshony et al.

(10) Patent No.: US 9,757,098 B2
(45) Date of Patent: Sep. 12, 2017

(54) MEDICAL DEVICE AND METHOD FOR USE IN TISSUE CHARACTERIZATION AND TREATMENT

(75) Inventors: Dan Hashimshony, Pardes Hana (IL); Gil Cohen, Jerusalem (IL); Iddo Geltner, Even Yehuda (IL)

(73) Assignee: DUNE MEDICAL DEVICES LTD., Caesarea (IL)

( * ) Notice: Subject to any disclaimer, the term of this patent is extended or adjusted under 35 U.S.C. 154(b) by 1045 days.

(21) Appl. No.: 13/547,950

(22) Filed: Jul. 12, 2012

(65) Prior Publication Data

US 2012/0316463 A1 Dec. 13, 2012

Related U.S. Application Data

(63) Continuation-in-part of application No. 12/663,923, filed as application No. PCT/IL2008/000965 on Jul. 13, 2008, now Pat. No. 9,301,734.

(Continued)

(51) Int. Cl.
A61B 10/02 (2006.01)
A61B 17/3205 (2006.01)
A61B 17/00 (2006.01)

(52) U.S. Cl.
CPC ...... *A61B 10/0275* (2013.01); *A61B 17/3205* (2013.01); *A61B 2017/00026* (2013.01);
(Continued)

(58) Field of Classification Search
CPC ............ A61B 10/0275; A61B 17/3205; A61B 2017/00057; A61B 2017/00039; A61B 2017/00026
See application file for complete search history.

(56) References Cited

U.S. PATENT DOCUMENTS 3,910,279 A * 10/1975 Okada .................... A61B 18/14
606/47
5,630,426 A * 5/1997 Eggers ................ A61B 5/0531
600/395

(Continued)

FOREIGN PATENT DOCUMENTS

WO WO 92/17108 A1 10/1992
WO WO 98/12968 4/1998

(Continued)

OTHER PUBLICATIONS

Jan. 24, 2013 Search Report issued in EP Application No. 12168882.4.

*Primary Examiner* — Sean Dougherty
(74) *Attorney, Agent, or Firm* — Browdy and Neimark, PLLC

(57) ABSTRACT

A medical device including a tissue characterization probe having an elongated carrier for carrying an array of tissue characterization sensors arranged in a spaced-apart relationship at least along an axis of said carrier within at least a distal portion thereof, such that progression of the probe through a tissue mass provides for locating and determining a dimension of an abnormal tissue specimen inside said tissue mass based on characterization signals from the sensors in the array. The elongated carrier has two integral portions including said distal portion and a hollow portion extending between a proximal end of the carrier and said distal portion. The carrier is configured for passing a predetermined treatment tool through the hollow portion thereof and enabling at least a part of the treatment tool to project from the hollow portion and extend along the distal portion.

19 Claims, 8 Drawing Sheets

Related U.S. Application Data

(60) Provisional application No. 60/950,081, filed on Jul. 16, 2007.

(52) U.S. Cl.
CPC ............... *A61B 2017/00039* (2013.01); *A61B 2017/00057* (2013.01)

(56) References Cited

U.S. PATENT DOCUMENTS

| | | | |
|---|---|---|---|
| 5,800,350 | A | 9/1998 | Coppleson et al. |
| 5,846,513 | A | 12/1998 | Carroll et al. |
| 6,006,755 | A | 12/1999 | Edwards |
| 6,022,362 | A * | 2/2000 | Lee .................... A61B 10/0275 600/564 |
| 6,120,437 | A | 9/2000 | Yoon et al. |
| 6,321,109 | B2 | 11/2001 | Ben-Haim et al. |
| 6,331,166 | B1 * | 12/2001 | Burbank .......... A61B 17/00491 600/567 |
| 6,419,635 | B1 | 7/2002 | Hedengren et al. |
| 6,419,640 | B1 | 7/2002 | Taylor |
| 6,440,147 | B1 * | 8/2002 | Lee et al. ...................... 606/159 |
| 6,689,145 | B2 | 2/2004 | Lee et al. |
| 6,780,179 | B2 * | 8/2004 | Lee .................... A61B 10/0266 606/159 |
| 6,813,515 | B2 | 11/2004 | Hashimshony |
| 7,101,378 | B2 * | 9/2006 | Salameh .......... A61B 17/32056 600/564 |
| 7,122,011 | B2 | 10/2006 | Clifford et al. |
| 7,184,824 | B2 | 2/2007 | Hashimshony |
| 8,413,582 | B1 | 4/2013 | Chen |
| 2001/0047169 | A1 | 11/2001 | McGuckin, Jr. et al. |
| 2001/0056236 | A1 | 12/2001 | Angelsen |
| 2002/0019597 | A1 | 2/2002 | Dubrul et al. |
| 2002/0035361 | A1 | 3/2002 | Houser et al. |
| 2003/0009110 | A1 * | 1/2003 | Tu et al. ........................ 600/547 |
| 2003/0050574 | A1 | 3/2003 | Krueger |
| 2003/0055423 | A1 | 3/2003 | Levinson |
| 2003/0138378 | A1 | 7/2003 | Hashimshony |
| 2004/0243018 | A1 | 12/2004 | Organ et al. |
| 2004/0255739 | A1 | 12/2004 | Clifford et al. |
| 2005/0203419 | A1 | 9/2005 | Ramanujam et al. |
| 2006/0235286 | A1 | 10/2006 | Stone et al. |
| 2006/0270942 | A1 | 11/2006 | McAdams |
| 2008/0039742 | A1 | 2/2008 | Hashimshony et al. |
| 2008/0287750 | A1 | 11/2008 | Hashimshony et al. |
| 2010/0168611 | A1 | 7/2010 | Hashimshony et al. |
| 2011/0034806 | A1 | 2/2011 | Hartov et al. |
| 2012/0323134 | A1 | 12/2012 | Cory |
| 2013/0072815 | A1 | 3/2013 | Hashimshony et al. |
| 2013/0177972 | A1 | 7/2013 | Green et al. |
| 2013/0267821 | A1 | 10/2013 | Hashimshony et al. |

FOREIGN PATENT DOCUMENTS

| | | |
|---|---|---|
| WO | WO 99/44506 A1 | 9/1999 |
| WO | WO 01/74252 A2 | 10/2001 |
| WO | WO 01/82998 A2 | 11/2001 |
| WO | WO 2006/103665 A2 | 10/2006 |
| WO | WO 2007/015255 A2 | 2/2007 |
| WO | WO 2007/083310 A2 | 7/2007 |
| WO | WO 2009/010960 A2 | 1/2009 |
| WO | WO 2011/016035 A1 | 2/2011 |

* cited by examiner

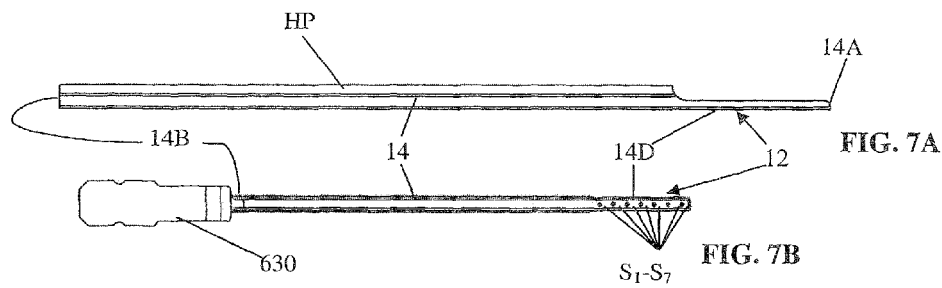
FIG. 7A
FIG. 7B
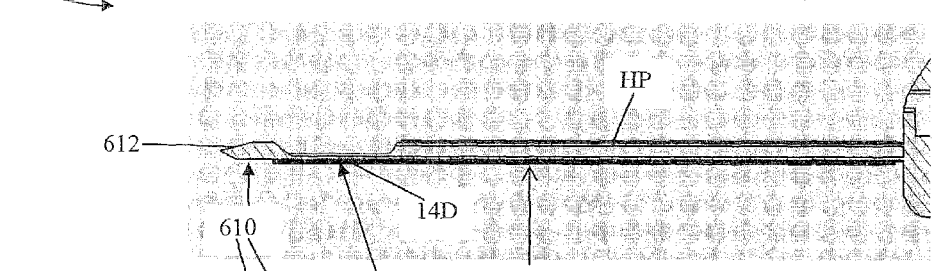
FIG. 7C
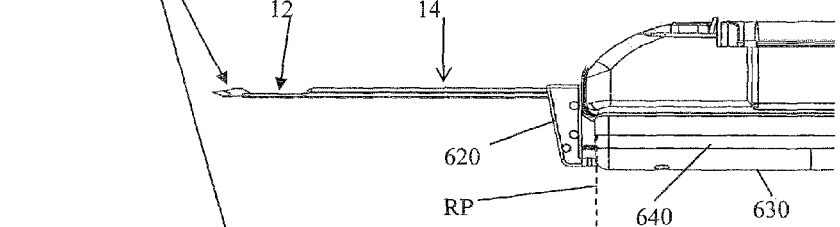
FIG. 7D
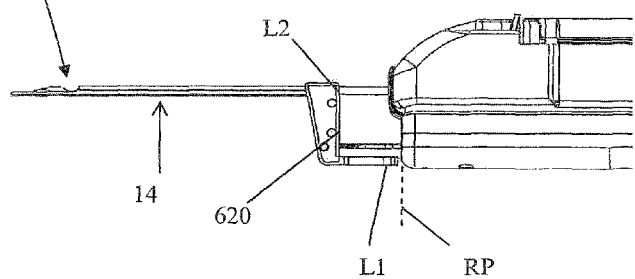
FIG. 7E

MEDICAL DEVICE AND METHOD FOR USE IN TISSUE CHARACTERIZATION AND TREATMENT

This is a new U.S. Continuation-in-Part Application of prior pending U.S. application Ser. No. 12/663,923, filed Dec. 10, 2009, which claims priority from PCT Application No. PCT/IL08/00965 filed Jul. 13, 2008 and Provisional U.S. Patent Application No. 60/950,081 filed on Jul. 16, 2007. The disclosure of each of the prior applications is hereby incorporated herein by reference in its entirety.

FIELD OF THE INVENTION

This invention relates to medical devices and methods for use in tissue characterization and treatment.

BACKGROUND

Techniques for in situ identifying abnormal (e.g. tumorous) cells in a biological tissue are generally known. Such techniques include those utilizing determination of the electrical properties of a tissue, for example, by determination of electrical impedance or dielectric constants. Some kinds of tumors can be identified by determining differences in the measured electrical properties of the tissue. The identified and located region of abnormal tissue can then be treated and/or removed from the body Various types of tissue characterization sensor and its integration with a tissue treatment/removal tool are described in the following patent publications, all assigned to the assignee of the present application: US2003138378, WO2006103665, WO2007015255, U.S. Pat. No. 6,813,515 and U.S. Pat. No. 7,184,824.

Also, various techniques are known for removing a certain tissue specimen from a tissue mass. These techniques are disclosed for example in U.S. Pat. No. 6,689,145 and U.S. Pat. No. 7,122,011.

GENERAL DESCRIPTION

There is a need in the art to facilitate precise location and determination of a volume of a tissue specimen (e.g. abnormal tissues) to be treated (e.g. removed). Also, there is need in the art for a tissue treatment technique capable of adjusting a treatment volume to the determined volume of the abnormal tissue specimen.

The present invention solves the above problems by providing a novel medical device for use in tissue characterization and treatment. The device comprises a tissue characterization probe comprising an elongated carrier for carrying an array of tissue characterization sensors arranged in a spaced-apart relationship at least along an axis of said carrier. During the progression of the probe through a tissue mass, signals from the tissue characterization sensors are used for locating and determining a dimension of an abnormal tissue specimen inside the tissue mass. This enables consequent or immediate treatment of the abnormal tissue specimen by a treatment tool.

The treatment tool may be configured for carrying out at least one of the following: biopsy, cutting, delivering physical treatment, delivering treatment medication, diagnostics. In some embodiments of the invention, the treatment tool is carried by (e.g. mounted on or inside) the characterization probe carrier. In some embodiments, the treatment tool may be selectively shiftable between its inoperative position being located substantially entirely inside the carrier and its operative position projecting by at least one tissue treating portion towards outside the carrier. The dimension of the tissue treating portion(s) projectable from the carrier, and possibly also location of the tissue treating portion(s) with respect to the carrier can be controllably varied.

In some embodiments of the invention, the probe carrier is formed with a guiding cutting tool, to facilitate insertion of the probe towards a targeted location in the tissue. Also, in some embodiments of the invention, a marker may be left in the body, at the location of the tissue being treated (removed).

As indicated above, in some embodiments of the invention, the treatment tool may be carried by the characterization probe. The configuration may be such that the treatment tool is an integral part of the medical device, or is removably mountable thereon (e.g., on the tissue characterization probe), for example allowing for subsequent changing between different kinds of treatment tools (such as cutting, biopsy, delivering physical treatment, delivering treatment medication, diagnostics), with relative ease and speed. The technique of the invention, enabling determination of the dimension of the abnormal tissue specimen, as well as consequent or immediate treatment of said specimen allows for precise, effective treatment even for very small and local tissue mass. Moreover, the technique may be even more precise when the treatment tool may be activated at the immediate vicinity of the sensors or at the exact location of an individual sensor, without moving the sensors from place.

Thus, according to one broad aspect of the invention, there is provided a medical device for use in tissue characterization and treatment, the device includes:

a tissue characterization probe including an elongated carrier for carrying an array of tissue characterization sensors arranged in a spaced-apart relationship at least along an axis of the carrier within at least a distal portion thereof, such that progression of the probe through a tissue mass provides for locating and determining a dimension of a tissue specimen inside the tissue mass based on characterization signals from the sensors in the array.

The elongated carrier has two integral portions including the above mentioned distal portion and a hollow portion extending between a proximal end of the carrier and the distal portion.

The elongated carrier is configured for passing a treatment tool through the hollow portion thereof and enabling at least a part of the treatment tool to project from the hollow portion and extend along the distal portion.

The device thereby enables consequent treatment of a tissue specimen by the treatment tool.

In some embodiments, the distal portion is configured as a trough like member thereby enabling concurrent alignment of a distal portion of the treatment tool at one side of the distal portion and the array of tissue characterization sensors at opposite side of the distal portion to the same segment of the tissue mass.

According to some embodiments, the carrier is configured and operable to enable the treatment tool to be selectively shiftable between its inoperative position being located substantially entirely inside the hollow portion of the carrier and its operative position projecting by its at least one tissue treating portion towards outside the carrier.

According to some other embodiments, the carrier is configured to allow movement of the tissue treating portion of the treatment tool with respect to the carrier along the axis of the array of tissue characterization sensors carried by the carrier.

The medical device of the present invention may be configured for carrying out at least one of the following treatment tools: biopsy tool, cutting tool, physical treatment tool, medication delivery tool, diagnostics tool.

The medical device may include a handle portion connectable to or integral with the proximal end of the carrier.

According to some embodiments, the medical device includes a movement mechanism located at the proximal end of the carrier, and being configured and operable to enable relative displacement between the carrier and the treatment tool. The movement mechanism may be located inside the handle.

In some embodiments, the movement mechanism includes a registration assembly to define a reference position for the array of tissue characterization sensors with respect to a certain reference plane defined by the device, thereby enabling to monitor repositioning of the tissue characterization sensors caused by movement of the carrier with respect to the reference plane.

According to some embodiments, the medical device includes a movement mechanism located at the proximal end of the carrier, and being configured and operable to enable relative displacement between the carrier and the treatment tool, the movement mechanism includes a registration assembly to define a reference position for the array of tissue characterization sensors with respect to a certain reference plane defined by the handle.

The registration assembly may include a L-like shaped bracket which by its one arm of a given length is movably connected to the handle and by its other arm is connected to the carrier, the reference plane being defined by a distal edge of the handle, thereby enabling to monitor repositioning of the tissue characterization sensors caused by movement of the bracket with respect to the reference plane.

According to some embodiments, the handle attached to the proximal side of the carrier is configured for engaging with a handle portion of the treatment tool when the treatment tool is being inserted into the hollow portion of the carrier.

According to another broad aspect of the present invention, there is provided a medical device configured as a two-part assembly including a first assembly carrying a tissue characterization probe and a second assembly carrying a treatment tool, the first and second assemblies being removably attachable to one another, wherein the tissue characterization probe includes an elongated carrier for carrying an array of tissue characterization sensors arranged in a spaced-apart relationship at least along a longitudinal axis of the carrier within at least a distal portion thereof, such that progression of the probe through a tissue mass provides for locating and determining a dimension of a tissue specimen inside the tissue mass based on characterization signals from the sensors in the array.

The elongated carrier has two integral portions including the distal portion and a hollow portion extending between a proximal end of the carrier and the distal portion and configured for passing of at least a part of the treatment tool through the hollow portion of the carrier while attaching the first and second assemblies of the medical device to one another.

According to some embodiments, the medical device further includes a control unit configured for receiving and analyzing tissue characterizing signals from each of all the sensors and utilizing data indicative of the respective sensors' location for determining a dimension of an abnormal tissue specimen, thereby enabling consequent treatment of the abnormal tissue specimen by a treatment tool.

In some embodiments, the control unit includes a graphical user interface configured for presenting information related to the signals received from all the sensors, thereby providing an operator with information regarding the tissue type at the locations of the sensors, and facilitating analysis of the location and extent of the tissue to be treated.

As described above, in some embodiments, the distal portion is configured as a trough like member enabling concurrent alignment of the distal portion of the treatment tool and the array of tissue characterization sensors with the same segment of the tissue mass. As also mentioned above, the treatment tool may be selectively shiftable between its inoperative position being located substantially entirely inside the hollow portion of the carrier and its operative position projecting by its at least one tissue treating portion towards the distal portion of the carrier.

According to some embodiments, the treatment tool and the carrier are configured to enable the treatment tool to be selectively shiftable between its inoperative position being located substantially entirely inside the hollow portion of the carrier and its operative position projecting by its at least one tissue treating portion towards outside the carrier when a part of the treatment tool extends along the distal portion of the carrier.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 7A-7E show one more example of the device configuration where a treatment tool can be applied to the desired location, identified by the tissue characterization sensors, while allowing the sensors to be kept in place;

DETAILED DESCRIPTION OF EMBODIMENTS

Figure 1:
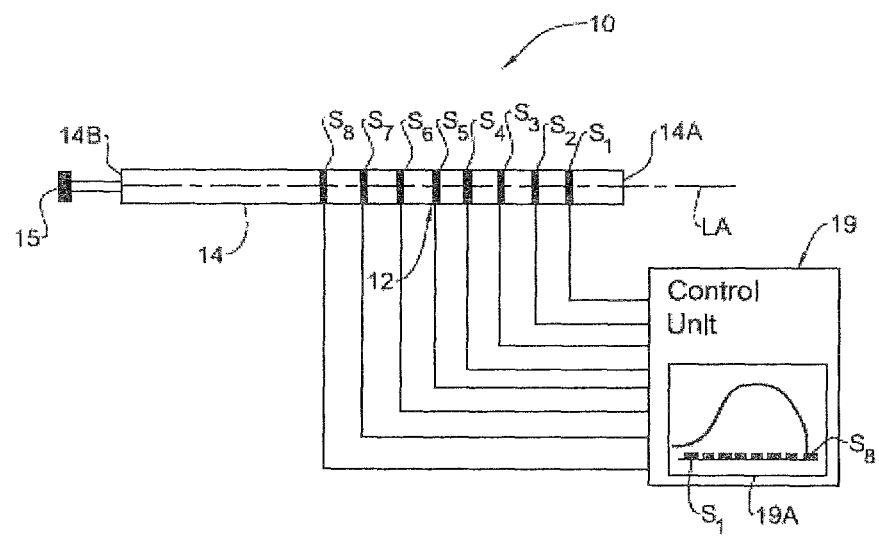
FIG. 1 is a schematic illustration of a medical device of the present invention.

Referring to FIG. 1, there is schematically illustrated a medical device, generally designated 10, according to an embodiment of the invention. The device 10 is configured for use in tissue characterization and treatment, and includes a tissue characterization probe 12 carried by an elongated shaft 14, which has distal and proximal ends 14A and 14B, respectively, and is formed with a control handle 15 at its proximal end 14B. The tissue characterization probe 12 includes an array of tissue characterization sensors, eight such sensors $S_1$-$S_8$ being shown in the present example.

The tissue characterization sensor array may include one or more of optical, radiofrequency (RF), microwave (MW), electrical, magnetic, temperature, elastic, biological, chemical, radioactive-emission, and mechanical sensors of any known type. The construction and operation of the tissue characterization sensor does not form part of the present invention, and therefore need not be specifically described.

For example, sensors described in the above indicated patent publications assigned to the assignee of the present application may be used.

The sensors $S_1$-$S_8$ are arranged in a spaced-apart relationship along a longitudinal axis LA of the carrier 14, and may be arranged in one- or two dimensional array. For example, the sensor array may include, in addition to a group of sensors arranged in one-dimensional array, sensors arranged in a spaced-apart manner along a circumferential region of the carrier. The sensor array gives, in real time, indication about the nature of tissue along the carrier 14.

The sensors are spaced along the axis LA from one another a known distance, which may or may not be equal for all the sensors in the array. The known relative locations of the sensors along the carrier 12 allows for identifying corresponding locations in a tissue mass when the probe is progressing through the tissue mass (i.e. scans the tissue) based on signals received from the sensors. In this connection, the medical device 10 is associated with an appropriate control system 19 configured for receiving and analyzing the signals generated by the sensors. It should be understood that connection between the sensors and the control unit is shown in the figure schematically, and in case wired connection is used such wires would extend inside the shaft 14 and exit at the proximal end 14B.

The control system may be an external system connectable (via wires or wireless signal transmission) to the sensors, or may be a constructional part of the probe itself. The control system, based on the analysis of the received signals, operates for determining a location of the margins of an abnormal tissue region inside the examined tissue mass and generating output data indicative of a dimension of the abnormal tissue region. This allows for consequent treatment of the abnormal tissue region by an appropriate treatment tool.

The control system preferably includes a graphical user interface (GUI) 19A, and is configured for presenting information related to the signals received from each of the sensors. This information provides the operator with information regarding the tissue type at the locations of the sensors. The information presented on the GUI may assist the operator in analyzing the location and extent of the tissue to be treated.

Generally, the treatment tool may be configured for carrying out one or more of the following: biopsy, cutting, delivering physical treatment, delivering treatment medication, diagnostics. More specifically, the present invention is used for removal of an intact tissue specimen (abnormal tissue) and is therefore described below with respect to this specific but not limiting example.

Preferably, the probe 12 also carries a treatment tool, e.g. a cutting tool. This is implemented by configuring the probe such that the treatment tool can be selectively shiftable between its inoperative position, when it is located substantially entirely inside the carrier 14, and its operative positions when its one or more excision elements (constituting one or more tissue treating elements) project(s) from the carrier.

In some examples of the invention, the selective projection of the excision element is achieved by using the treatment tool of a kind known in the art, where the excision element projects from the carrier body through an opening made along the body portion while moving with respect to the carrier along an axis inclines with respect to the axis LA. In some other examples, the excision element projects from the carrier (e.g. from its distal end) while moving with respect to the carrier substantially along the axis LA. Such configurations are also generally known in the art. The treatment tool may be configured with a removed tissue collecting unit, which may or may not be selectively projectable from the probe.

According to the invention, the medical device is configured such that a dimension of the excision element part projecting from the carrier can be controllably adjusted (varied) in accordance with the determined dimension of the abnormal tissue margins, thereby adjusting the excision volume. Preferably, the excision element is configured for both cutting the tissue and collecting the tissue being cut.

The following are some specific but not limiting examples of the configuration of the device of the present invention. The same reference numbers are used for identifying components that are common in all the examples.

Figure 2:
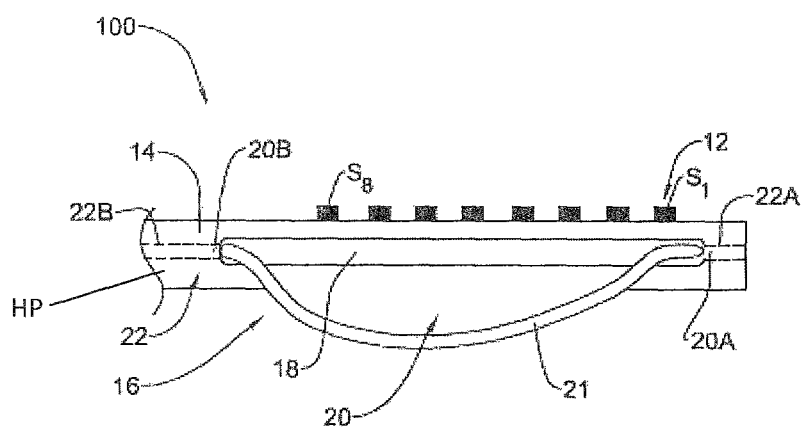
FIGS. 2 to 6 show five examples, respectively, of the device configuration for both the tissue characterization and removal of a tissue specimen.

FIG. 2 shows a medical device 100 for treatment of a tissue specimen, e.g. for removal of an intact tissue specimen. The device 100 includes an elongated shaft/carrier 14 on which sensors $S_1$-$S_8$ of a tissue characterization probe 12 are mounted in spaced-apart locations, and a tissue cutting tool (generally, a treatment tool) 16 mounted on the carrier 14. In this specific not limiting example, the carrier 14 has a hollow body HP (of a cylindrical-like shape) and the treatment tool 16 (cutting tool) is insertable into said hollow body HP.

The cutting tool 16 has a body portion 22 located inside the body HP of the carrier 14, and an excision element 20 projectable from the body 22 through an opening 18 made in the hollow body HP of the carrier 14. In the figure, the excision element 20 is shown in its operative projecting state. The excision element has a cutting edge 21, and may be configured to have a cup-like shape when in the projecting state, thereby enabling collection of tissue while being cut during the rotation of the carrier 14 and thus of the excision element 20.

The excision element 20 extends between its first and second ends 20A and 20B which are attached to respective first and second locations on the treatment tool body 22 and spaced-apart along the axis LA of the carrier 14. The treatment tool is configured to enable a controllable change of the dimensions of the excision element 20. In the present example, this is implemented by making the treatment tool body 22 from two spaced members 22A and 22B, where at least one of them is slidable with respect to the other along the carrier axis LA. As a result, a distance between the first and second locations, and accordingly the first and second ends 20A and 20B of the excision element, changes, thereby enable adjustment of the dimension of the cutting portion 21 projecting through the carrier 14.

By controlling the location of the excision element distal and proximal ends 20A and 20B along the carrier 14, and thus controlling the excision volume, a user can perform optimal removal of a tissue specimen, for example during a breast biopsy procedure. The entire excision element 20 may be movable along the body 22. Thus, the excision volume is controlled by user by changing the location of the excision element 20 along the carrier 14 and changing a distance between the distal and proximal ends of the excision element.

Figure 3:
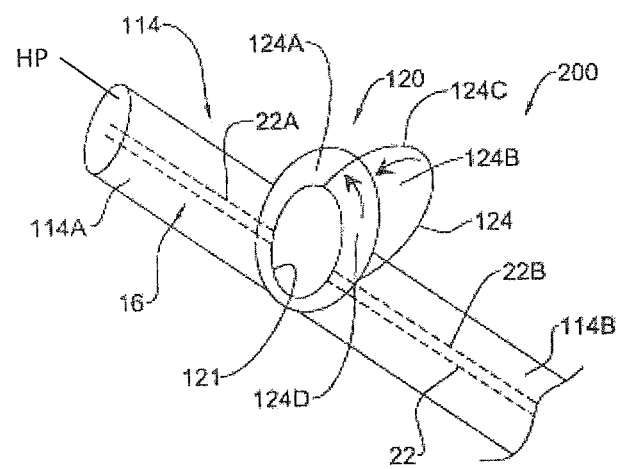

In the above example, the tissue removal procedure is carried while rotating the carrier 14. Such procedure can be performed while keeping the carrier position and rotating the treatment tool. This is exemplified in FIG. 3. A device 200 includes a carrier 114 formed by two separate parts 114A and 114B kept together by a treatment tool 16 inside the carrier 114. The treatment tool 16 has a body part 22 formed by two spaced-apart members 22A and 22B, and an excision element 120 attached thereto by its distal and proximal ends 20A and 20B. The excision element 120 has a semi-spherical surface 124 defining a cutting edge 21. The surface 124 has two arc-like portions 124A and 124B movable along the axis LA such that when they move towards one another one of the portions 124A becomes received by the other portion 124B. Also, the surface 124 has two parts 124C and 124D separately movable such that portion 124C can be received by portion 124C. These movements allow for altering the excision volume when in the operative projecting state of the excision element 120 and for shifting the element 120 between its operative projecting position and its inoperative position being located inside the carrier 14. Cutting is implemented while rotating the tool body 22 with respect to the carrier 14. Also, this configuration allows for collecting the tissue specimen while being cut.

Figure 4:
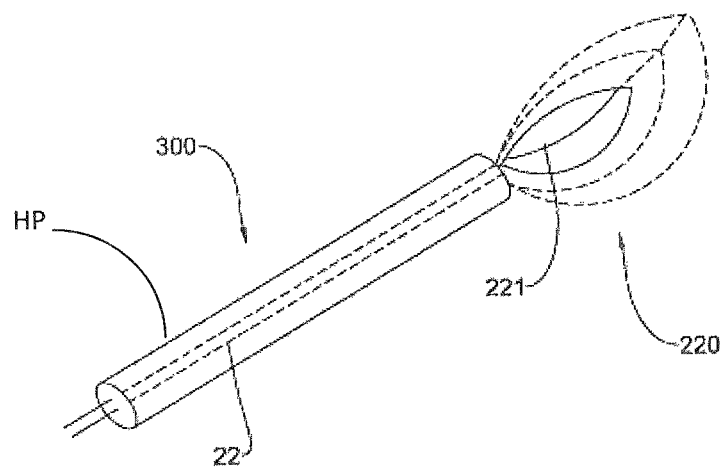

FIG. 4 shows a medical device 300 according to yet another example of the invention. Here, a treatment tool 216 has a body shaft 22 carrying at its distal end an excision element 220. The latter may or may not be integral with the body shaft 22. The excision element has a closed-loop cutting edge 221 which is pre-bent at fabrication so as to deploy from its inoperative closed position when inside the carrier 14 into an open ring-like shape when being projected from the carrier. Attached to the cutting edge 221 is a flexible tissue collecting unit. When the excision element is pushed (by user) out of the carrier 14 through its distal end, it gradually passes through its different operative states being of a spoon-like shape of different dimensions.

Figure 5:
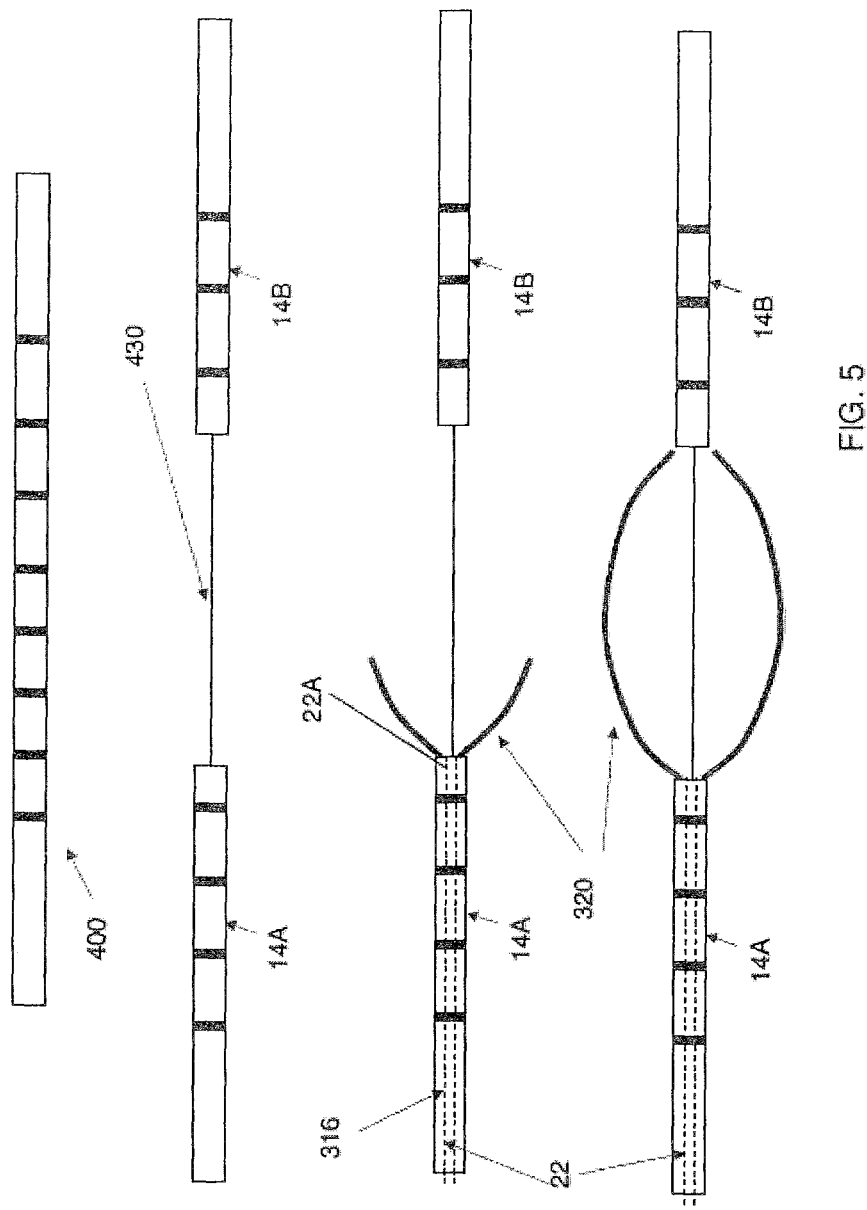

FIG. 5 shows a medical device 400 according to yet another example of the invention. Here, an elongated shaft (carrier) 14 is separable into two sections 14*a* and 14*b*, which remain connected to each other by a wire or shaft 430. A treatment tool 316 located inside the carrier 14 has a body shaft 22 carrying at its distal end 22A excision elements 320. The latter may or may not be integral with the body shaft 22. The treatment tool shaft 22 is advanced inside the shaft 14 until its distal end 22A reaches the distal end of the section 14A. Excision elements 220 are then deployed so as to excise an intact tissue portion.

Figure 6:
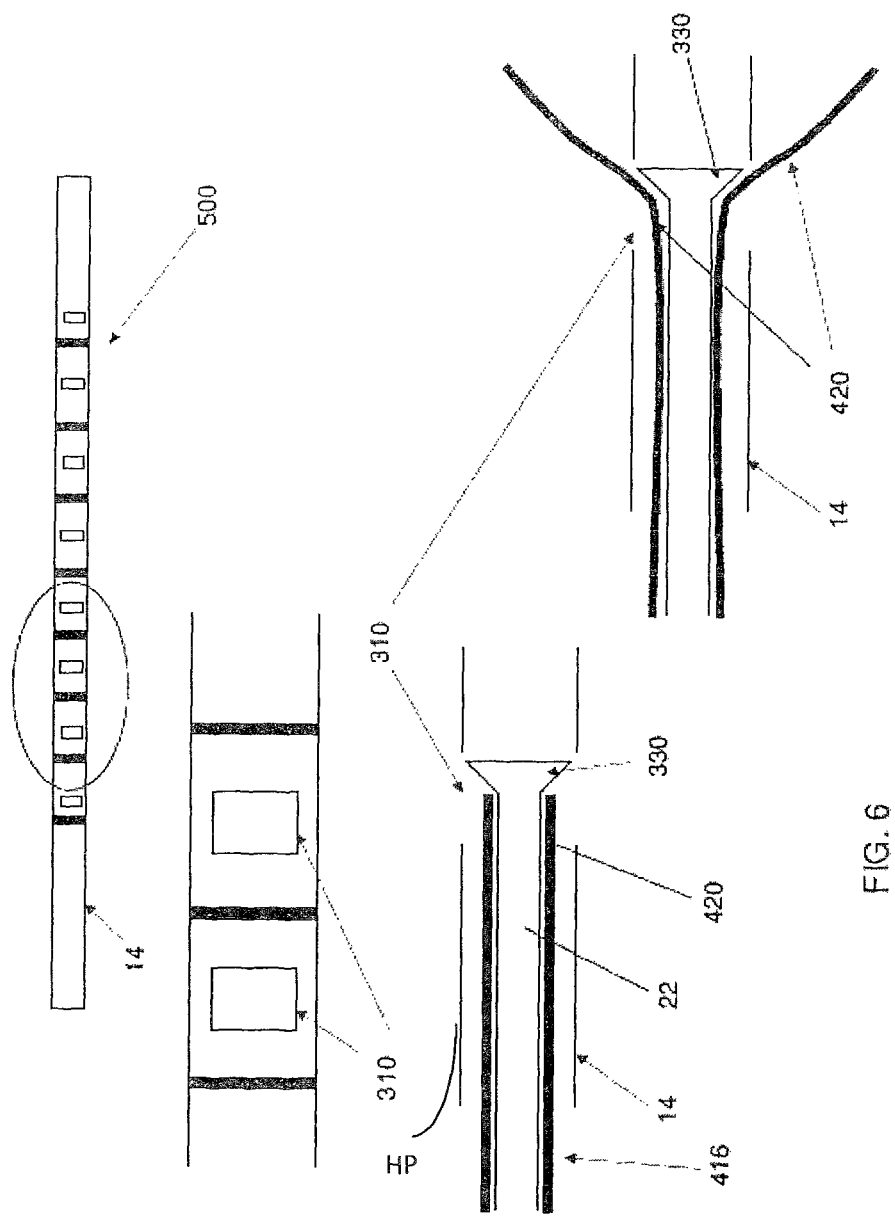

FIG. 6 shows a medical device 500 according to yet another example of the invention. Here, peripheral slots 310 are provided in the shaft/carrier 14 being interspaced between tissue characterization sensors. At each location along the shaft 14 there may be 2-8 peripheral slots. A treatment tool 416 has a body shaft 22 carrying at its distal end excision elements 420. The latter may or may not be integral with the body shaft 22. A number of excision elements 320 corresponds to the number of the slots 310. The treatment tool 416 is advanced inside the shaft 14 until its distal end is positioned at a specific slot 310 location. The distal end of the treatment tool shaft 22 has a tapered/angled ending portion 330. This ending portion allows for controlling an angle at which the excision elements 420 is extended from the shaft 14 into tissue. The excision elements 420 are pre-bent so that when extended they close back on the shaft 14, thus cutting the tissue portion adjacent to the shaft 14. Additionally, the excision elements 420 may be connected at their ends by wires, or other flexible connection. This connection can be manipulated to induce the contraction of the excision elements 420 towards shaft 14, to facilitate cutting of the tissue portion adjacent to the shaft 14.

Reference is now made to FIGS. 7A-7E which show a medical device 600 according to one more example of the present invention. The device 600 is configured for use in tissue characterization and treatment, and includes a tissue characterization probe 12 carried by an elongated shaft/carrier 14 and is configured for carrying a treatment tool 610. The carrier 14 has distal and proximal ends 14A and 14B, and has two integral portions, i.e. a hollow portion HP (of a cylindrical-like shape) extending from proximal end 14B and a trough-like portion (or an open-cut portion) 14D extending from said hollow portion towards the distal end 14A. As will be described below, the treatment tool when attached to/mounted on the medical device is at least partially located inside the hollow portion HP and either permanently or selectively (when required) projectable from the hollow portion HP such that a part of the treatment tool extends along the trough portion 14D to be exposed to the tissue. The hollow portion HP may have a thin wall configuration, so it does not add any remarkable thickness to the treatment tool passing through it, which in turn enhances the convenience in using and inserting the device 600 into a subject's body. The tissue characterization probe 12 includes an array of spaced-apart tissue characterization sensors, seven such sensors $S_1$-$S_7$ being shown in the present example in FIG. 7B. The sensors are located on an external side (bottom side) of the trough portion 14D (there may be additional sensors extending along the hollow portion, which are not specifically shown), while the opposite, internal side of the trough portion 14D serves as a site for locating a portion of the treatment tool while in an operative position thereof.

It should be noted that the sensors may be thin, and thus do not protrude too much from the outer surface of the carrier/trough's part 14D, consequently further enhancing the effectiveness and convenience in using the device inside the subject's body. Such thin and possible flexible sensor structures are described for example in WO 2011/016035, which is assigned to the assignee of the present application and which is incorporated herein by reference. According to this technique, a sensor unit/structure includes a near field electromagnetic sensor and a flexible signal transmission structure, which are integral with one another by means of one or more common continuous surfaces. The flexible signal transmission structure may be constructed from a first layer including signal connection lines associated with sensor cells of the near field electromagnetic sensor and a second electrically conductive layer electrically coupled to the electrically conductive material of the sensor.

It should be understood that the treatment tool portion may or may not be physically supported by the internal side of the trough portion 14D. Thus, the treatment tool portion, and accordingly a tissue segment accessed by the treatment tool, can be concurrently aligned with the sensors, enabling the treatment procedure to be carried out without a need to displace the sensing portion of the device. Thus, the array of sensors is located at the distal part 14D of the elongated shaft 14, and this distal part 14D forms the trough portion of the device which concurrently exposes both the sensors and the treatment tool to the same part/segment of the tissue. It can be appreciated that the device 600 enables immediate treatment or acquisition of very small tissue mass at the exact location of any one of the sensors, during scanning of a tissue mass and without any need for moving the sensors from place as may be required with the above-described device 400 for example.

As shown in FIGS. 7C-7E, the device 600 may include a tissue cutting tool 610 (constituting a treatment tool) being carried and housed inside the proximal hollow portion HP of the shaft 14 and projecting therefrom and extending above the distal, trough portion 14D. The shaft 14 and the cutting tool 610 mounted therein can move forwards and backwards relative to each other. The excision element 612 (constituting a treatment tool portion) of the cutting tool 610 is in its operative position when it is located above the trough part 14D or at least partially extends beyond it forwardly into the tissue mass being treated. It should be noted that any suitable cutting tool that conforms to the shape and dimensions of the carrier 14 can be used and the invention is not limited to the cutting tool 610 being shown in this specific example, and any other cutting tool as well as any other treatment tools can be used, such as a tool for delivering treatment medication.

The device 600 is typically configured as a hand-held device having a handle portion 630 at the proximal end 14B of the carrier 14 (FIG. 7B). Further, the device 600 may include a movement mechanism located at the proximal end 14B of the carrier 14, enabling relative displacement between the carrier 14 and the treatment tool 610. The movement mechanism may be manually activated by user and/or may be assisted by a motor unit 640. The movement mechanism (e.g. the motor unit) may be mounted inside the handle.

The motor unit 640 drives a movement of the shaft 14 relative to the treatment tool (cutting tool) 610 forwards and backwards as shown in FIGS. 7E and 7D, allowing for covering, revealing or repositioning the cutting tool 610 during the treatment process. FIGS. 7D and 7E exemplify two different relative positions of the carrier and the treatment tool. In this specific but not limiting example, the configuration is such that the carrier 14 moves with respect to the treatment tool 610. In the example of FIG. 7D, the carrier 14 is in its retracted position (retracted towards the handle) exposing a longer portion of the treatment tool to the tissue mass, as compared to the extracted position of the carrier 14 shown in FIG. 7E, where a shorter portion of the tissue tool is exposed.

Possibly, the movement mechanism (either manual or driven by motor) includes a registration assembly to define a reference/registration position for the sensors' array with respect to a reference plane, which may be defined by the handle location. This assists in accurate determination of the dimension of an abnormal tissue specimen that is to be treated. The registration assembly may be formed by an L-like shaped bracket which by its one arm L1 of a given length is movably (telescopically) connected to the handle 630 and by its other arm L2 is connected to the carrier. Thus, when the arm L1 moves towards and away from a reference plane RP defined by the distal edge of the handle 630 (via a respective guiding mechanism which is not specifically shown) between its retracted and extracted positions with respect to the handle, the carrier 14 becomes correspondingly movable towards and away from the handle. Such configuration assists in monitoring the sensors' repositioning caused by the movement of the carrier which is in turn controlled by the movement of the bracket 620 with respect to the reference plane RP. It should be noted, that the reference plane RP can be defined at another point along the device, and it is not limited to the shown in FIGS. 7D-E, in any case the calculations of distances are adapted to the reference plane chosen.

Figure 8A:
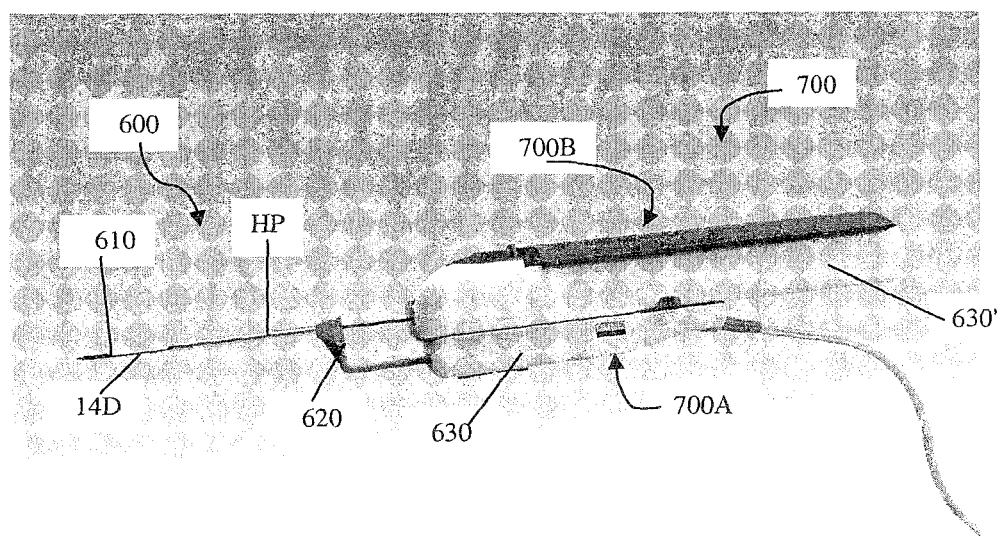
FIGS. 8A-8B show one configuration of a tissue treatment apparatus utilizing the medical device of the present invention.
Figure 8B:
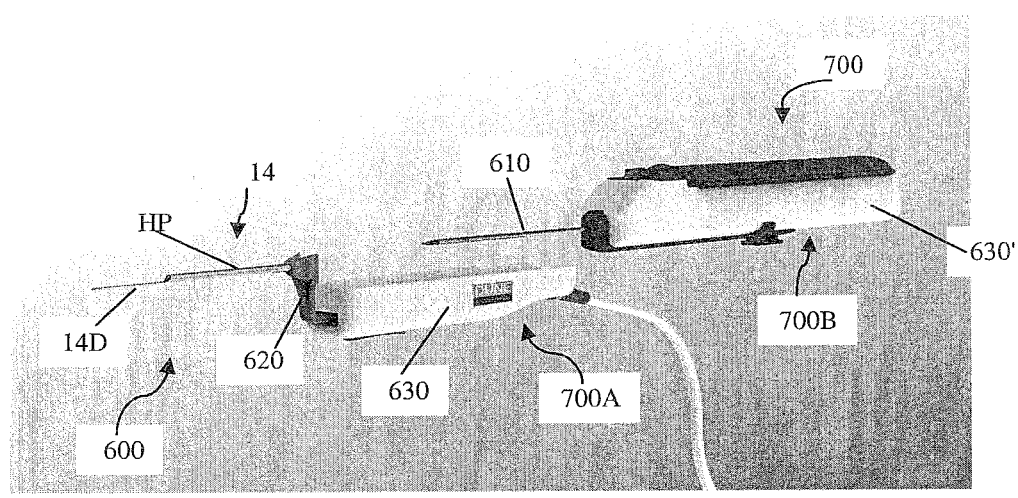
Figure 9:
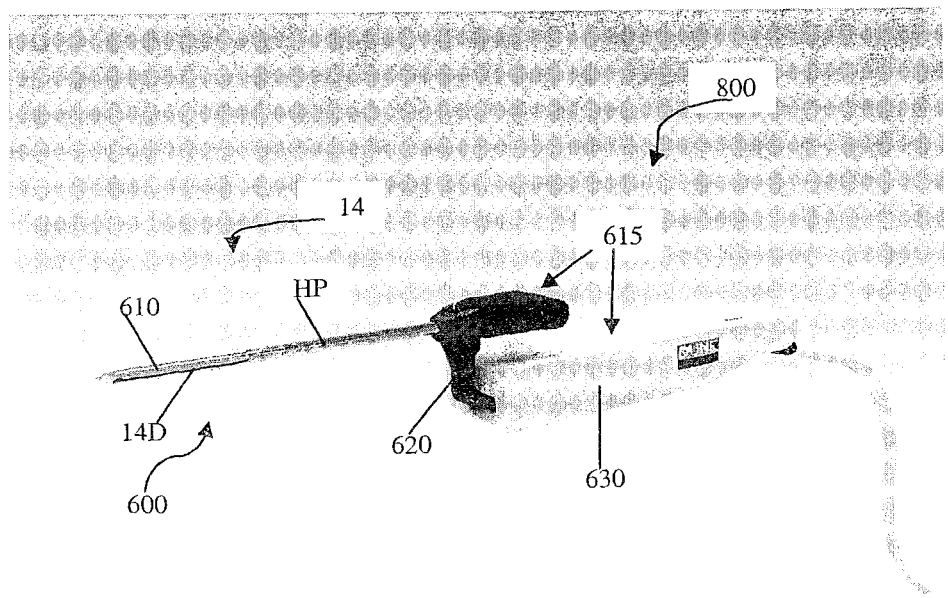
FIG. 9 shows a second configuration of a tissue treatment apparatus utilizing the medical device of the present invention.

Reference is now made to FIGS. 8A-8B and 9 showing two different configurations of a tissue treatment apparatus utilizing the medical device of the present invention.

In the example of FIGS. 8A-8B, the apparatus, generally designated 700, is configured as a two-part assembly. As better seen in FIG. 8B, the device 600 carrying the tissue characterization probe of the invention is associated with part 700A, while a treatment tool is carried by the part 700B. More specifically, the tissue characterization device 600 is mounted on a handle 630, e.g. via the registration assembly 620, and the treatment tool 610 is mounted on a handle 630'. The two parts 700A and 700B are configured to engage with one another as shown in FIG. 8A. The engagement is implemented by insertion of the treatment tool 610 into the hollow portion HP of the carrier 14 (FIG. 8B) and in the engaged position the handles 630 and 630' are aligned with one another. A suitable locking mechanism may be provided (not shown) securing the engaged position of the handles 630 and 630' during the apparatus operation thus allowing only the movement of the carrier 14 via the movement of the bracket 620 as described above. It should be noted that the device 600 of the invention may be designed (i.e. the carrier 14) so as to match the configuration of a suitable/desired treatment tool.

In the example of FIG. 9, the tissue treatment apparatus, designated 800, includes the above-described tissue characterization device 600 which in this specific but not limiting example is mounted on a handle 630 via a bracket 620 associated with an appropriate movement mechanism 615 (which may be manual, automatic, or a combination of both). The bracket 620 may be movable with respect to the reference plane defined by the distal edge of the handle causing a controllable movement of the carrier 14 with respect to the treatment tool 610.

It should however be noted that for some applications, e.g. in sterile conditions or for disposable usage, the treatment apparatus described may not use any handle and thus may be formed solely by the device 600 (i.e. the carrier 14 configured as exemplified above) and bracket 620. Alternatively, bracket 620 may be configured so as to enable connection and disconnection of bracket 620 from the handle 630. This also allows the device 600 (i.e. the carrier 14 configured as exemplified above) and bracket 620 to be disposable and/or sterile one.

It should be understood that in all the above-exemplified embodiments the device may be rotated, manually or mechanically, to assist in complete tissue treatment (e.g. cutting and removal). The removal/acquisition of relevant tissue portion may be carried out manually or by using a suctioning mechanism possibly implemented in the apparatus, e.g. in the handle 630'. The removed tissue is suctioned through the portion HP of the carrier 14 and out of the body, to be further treated as desired.

Thus, the present invention provides a novel medical device capable of precisely locating a tissue volume to be treated (removed), and also provides for treating (removing) the tissue by an integral treatment tool.

The invention claimed is:

1. A medical device for use in tissue characterization and treatment, the device comprising:
   an elongated carrier having a longitudinal axis, proximal and distal ends, and
   two integral portions extending along said longitudinal axis, from said proximal end to said distal end of the elongated carrier, said two integral portions including a cylindrical-like hollow proximal portion and a distal portion, said hollow proximal portion extending between said proximal end of the elongated carrier and said distal portion, said distal portion extending between said hollow proximal portion and said distal end of the elongated carrier, said elongated carrier carrying an array of spaced-apart tissue characterization sensors comprising tissue characterization sensors arranged on said distal portion of the elongated carrier, such that progression of the elongated carrier through a tissue mass provides for locating and determining a dimension of a tissue specimen inside said tissue mass based on characterization signals from the sensors in the array,
wherein
said distal portion is open-cut both along a length of said distal portion at least opposite to said tissue characterization sensors arranged on the distal portion, and along a full transverse section of the distal portion at said distal end of the elongated carrier,
said elongated carrier being thereby configured for passing a treatment tool through said hollow proximal portion and enabling at least a distal part of the treatment tool to project from the hollow proximal portion and to extend forwardly on the longitudinal axis, along said distal portion and beyond said open distal end of the elongated carrier,
the device thereby enabling consequent treatment of a tissue specimen by the treatment tool while keeping the elongated carrier in place.

2. A device according to claim 1, wherein said open-cut distal portion is configured as a trough like member enabling concurrent alignment of the distal part of the treatment tool at an internal side of the distal portion of the elongated carrier and at least one sensor of the array of tissue characterization sensors at an external side of the distal portion of the elongated carrier, with respect to one segment of the tissue mass.

3. A device according to claim 2, wherein said carrier is configured and operable to enable the treatment tool to be selectively shiftable between an inoperative position of the treatment tool, being located substantially entirely inside said hollow proximal portion of the carrier, and an operative position of the treatment tool, projecting forwardly on the longitudinal axis by at least one tissue treating portion of the treatment tool along said distal portion and beyond said open distal end of the elongated carrier.

4. A device according to claim 3, wherein the carrier is configured to allow movement of the tissue treating portion of the treatment tool with respect to the carrier along a direction on which the sensors are arranged.

5. A device according to claim 3, wherein said medical device is configured to carry out at least one of the following treatment tools: biopsy tool, cutting tool, physical treatment tool, medication delivery tool, diagnostics tool.

6. A device according to claim 1, comprising a handle portion connectable to or integral with the proximal end of the carrier.

7. A device according to claim 1, comprising a movement mechanism located at the proximal end of the carrier, and being configured and operable to enable relative displacement between the carrier and the treatment tool.

8. A device according to claim 6, comprising a movement mechanism located inside the handle, and being configured and operable to enable relative displacement between the carrier and the treatment tool.

9. A device according to claim 7, wherein the movement mechanism comprises a registration assembly to define a reference position for the array of tissue characterization sensors with respect to a certain reference plane defined by the device, thereby enabling to monitor repositioning of the tissue characterization sensors caused by movement of the carrier with respect to the reference plane.

10. A device according to claim 6, comprising a movement mechanism located at the proximal end of the carrier, and being configured and operable to enable relative displacement between the carrier and the treatment tool, the movement mechanism comprising a registration assembly to define a reference position for the array of tissue characterization sensors with respect to a certain reference plane defined by the handle.

11. A device according to claim 10, wherein the registration assembly comprises an L-like shaped bracket, wherein said bracket comprises one arm of a given length movably connected to the handle and another arm connected to the carrier, the reference plane being defined by a distal edge of the handle, thereby enabling to monitor repositioning of the tissue characterization sensors caused by movement of the bracket with respect to the reference plane.

12. A device according to claim 6, wherein the handle is configured for engaging with a handle portion of the treatment tool when the treatment tool is being inserted into the hollow proximal portion of the carrier.

13. A device according to claim 1 configured as a two-part assembly comprising a first assembly carrying said elongated carrier and a second assembly carrying said treatment tool, the first and second assemblies being removably attachable to one another, wherein said elongated carrier is configured for passing of at least a part of the treatment tool through the hollow proximal portion of the elongated carrier and for locating at least a distal part of the treatment tool above said distal portion or beyond said distal open end, while attaching the first and second assemblies of the device to one another.

14. A device of claim 13, comprising a control unit configured for receiving and analyzing tissue characterizing signals from each of all the sensors and utilizing data indicative of the respective sensors' location for determining a dimension of an abnormal tissue specimen, thereby enabling consequent treatment of the abnormal tissue specimen by a treatment tool.

15. A device according to claim 14, wherein the control unit comprises a graphical user interface configured for presenting information related to the signals received from all the sensors, thereby providing an operator with information regarding the tissue type at the locations of the sensors, and facilitating analysis of the location and extent of the tissue to be treated.

16. A device according to claim 13, wherein said distal portion is configured as a trough like member thereby enabling concurrent aligning a distal portion of the treatment tool projecting from the hollow portion at one side of the distal portion and the array of tissue characterization sensors at opposite side of the distal portion, with respect to one segment of the tissue mass.

17. A device according to claim 16, wherein the treatment tool and the carrier are configured to enable the treatment tool to be selectively shiftable between an inoperative position being located substantially entirely inside said hollow portion of the carrier and an operative position projecting by at least one tissue treating portion of the treatment tool towards the distal portion of the carrier.

18. A device according to claim 13, wherein said device is configured to carry out at least one of the following treatment tools: biopsy tool, cutting tool, physical treatment tool, medication delivery tool, diagnostics tool.

19. A device according to claim 16, wherein treatment tool and the carrier are configured to enable the treatment tool to be selectively shiftable between an inoperative position being located substantially entirely inside said hollow portion of the carrier and an operative position projecting by at least one tissue treating portion of the treatment tool towards outside the carrier when a part of the treatment tool extends along the distal portion of the carrier.

\* \* \* \* \*